US007994212B2

(12) United States Patent
Bissery

(10) Patent No.: US 7,994,212 B2
(45) Date of Patent: Aug. 9, 2011

(54) METHOD OF TREATING CANCER WITH DOCETAXEL AND DOXORUBICIN

(75) Inventor: Marie-Christine Bissery, Vitry Sur Seine (FR)

(73) Assignee: Aventis Pharma S.A., Antony (FR)

(*) Notice: Subject to any disclaimer, the term of this patent is extended or adjusted under 35 U.S.C. 154(b) by 1401 days.

(21) Appl. No.: 10/747,206

(22) Filed: Dec. 30, 2003

(65) Prior Publication Data

US 2004/0152642 A1 Aug. 5, 2004

Related U.S. Application Data

(60) Continuation of application No. 10/422,823, filed on Apr. 25, 2003, which is a continuation of application No. 09/705,739, filed on Nov. 6, 2000, now abandoned, which is a division of application No. 09/506,902, filed on Feb. 18, 2000, now Pat. No. 6,239,167, which is a division of application No. 09/371,520, filed on Aug. 10, 1999, now Pat. No. 6,214,863, which is a continuation of application No. 09/182,900, filed on Oct. 30, 1998, now abandoned, which is a division of application No. 08/967,036, filed on Nov. 10, 1997, now Pat. No. 5,908,835, which is a division of application No. 08/424,470, filed as application No. PCT/FR93/01096 on Nov. 8, 1993, now Pat. No. 5,728,687.

(30) Foreign Application Priority Data

Nov. 10, 1992 (FR) ..................................... 92 13525

(51) Int. Cl.
*A01N 43/02* (2006.01)
*A61K 31/436* (2006.01)

(52) U.S. Cl. .......................... 514/449; 514/283; 540/478

(58) Field of Classification Search ........................ None
See application file for complete search history.

(56) References Cited

U.S. PATENT DOCUMENTS

| 4,206,221 A | 6/1980 | Miller et al. |
| 4,814,470 A | 3/1989 | Colin et al. |
| 4,857,653 A | 8/1989 | Colin et al. |
| 4,876,399 A | 10/1989 | Holton et al. |
| 4,892,735 A | 1/1990 | Harrap |
| 5,015,744 A | 5/1991 | Holton |
| 5,136,060 A | 8/1992 | Holton |
| 5,229,526 A | 7/1993 | Holton |
| 5,254,580 A | 10/1993 | Chen et al. |
| 5,262,409 A | 11/1993 | Margolis et al. |
| 5,294,637 A | 3/1994 | Chen et al. ..................... 514/559 |
| 5,294,737 A | 3/1994 | Ojima |
| 5,466,834 A | 11/1995 | Holton |
| 5,476,954 A | 12/1995 | Bourzat et al. |
| 5,494,683 A | 2/1996 | Liversidge et al. |
| 5,532,388 A | 7/1996 | Bouchard et al. ............. 549/510 |
| 5,645,988 A | 7/1997 | Vande Woude et al. |
| 5,728,687 A | 3/1998 | Bissery |
| 5,814,658 A | 9/1998 | Bouchard et al. ............... 514/49 |
| 5,908,835 A | 6/1999 | Bissery |
| 6,214,863 B1 | 4/2001 | Bissery |
| 6,239,167 B1 | 5/2001 | Bissery |
| 6,441,026 B1 | 8/2002 | Bissery |

FOREIGN PATENT DOCUMENTS

| EP | 0317401 | 5/1989 |
| EP | 738 253 | 6/1995 |
| EP | 0 827 745 A1 | 3/1998 |
| EP | 0 827 745 B1 | 3/1998 |
| EP | 0 982 028 A1 | 3/2000 |
| WO | WO 92/09589 | 6/1992 |
| WO | WO 92/19765 | 11/1992 |
| WO | WO 94/10995 | 5/1994 |
| WO | WO 94/13654 | 6/1994 |
| WO | WO 94/13655 | 6/1994 |
| WO | WO 97/38731 | 10/1997 |
| WO | WO 99/31140 | 6/1999 |

OTHER PUBLICATIONS

Guéritte-Voegelein et al., "Relationships between the Structure of Taxol Analogues and Their Antimitotic Activity," *J. Med. Chem.* 34:992-998 (1991).
Commerçon et al., "Tetrahedron Letters," 33(36):5185-5188 (1992).
Chen et al., "Serendipitous Synthesis of a Cyclopropane-Containing Taxol Analog Via Anchimeric Participation of an Unactivated Angular Methyl Group," *J. Org. Chem.*, 58:4520-4521 (1993).
Klein et al., "Synthesis of Ring B-Rearranged Taxane Analogs," *J. Org. Chem.*, 59: 2370-2373 (1994).
Rowinsky, E., et al., "The Clinical Pharmacology and Use of Antimicrotubule Agents in Cancer Chemotherapeutics," *Pharmac. Ther.*, vol. 52, pp. 35-84 (1991).
Rowinsky, E. et al., "Sequences of Taxol and Cisplatin: A Phase I and Pharmacologic Study," *J. of Clin. Oncology*, vol. 9, No. 9, pp. 1692-1703 (1991).
Bissery, M., et al., Abstract 2645, *Proceedings of the AACR*, vol. 33, p. 443 (Mar. 1992).
Bissery, M., et al., "Preclinical Profile of Docetaxel (Taxotere): Efficacy as a Single Agent and in Combination," *Seminars in Oncology*, vol. 22, No. 6 (Suppl 13), pp. 3-16 (1995).
Bissery, M., et al., Abstract 1599, "Preclinical In Vivo Activity of Docetaxel Containing Combinations," *Proceedings of ASCO*, vol. 14, p. 489 (1995).
Bissery, M., et al., "The Taxoids," *Cancer Therapeutics: Experimental and Clinical Agents*, Chapter 8, pp. 175-193 (1997).
Mirabelli, C., et al., "A Murine Model to Evaluate the Ability of In Vitro Clonogenic Assays to Predict the Response to Tumors In Vivo," *Cancer Res.*, vol. 48, pp. 5447-5454 (1988).
Llombart-Cussac, A., et al., Proceedings of ASCO, vol. 16 (1997), Abstract No. 629.

(Continued)

Primary Examiner — Irene Marx
(74) Attorney, Agent, or Firm — Finnegan, Henderson, Farabow, Garrett & Dunner LLP

(57) ABSTRACT

Antitumor combinations comprising a taxane and at least one antibiotic for treating neoplastic diseases are described.

18 Claims, No Drawings

OTHER PUBLICATIONS

Gelmon, K., et al., "Phase I Dose-Finding Study of a New Taxane, RPR 109881A, Administered as a One-Hour Intravenous Infusion Days 1 and 8 to Patients with Advanced Solid Tumors," *Journal of Clin. Oncology*, vol. 18, No. 24, pp. 4098-4108 (2000).

Kurata, T., et al., "Phase I and Pharmacokinetic Study of a New Taxoid, RPR 109881A, Given as a 1-Hour Intravenous Infusion to Patients with Advanced Solid Tumors," *Journal of Clin. Oncology*, vol. 18, No. 17, pp. 3164-3171 (2000).

Budavari, S., et al., "Docetaxel," "The Merck Index, 13th Edition," *Merck Research Laboratories*, 3431, pp. 597-598, "Paclitaxel", p. 1251 (Ed. 2001).

Hartley-Asp, B., "Estramustine-Induced Mitotic Arrest in Two Human Prostatic Carcinoma Cell Lines DU 145 and PC-3," *The Prostate*, vol. 5, pp. 93-100 (1984).

Horwitz, S., et al., "Taxol: A New Probe for Studying the Structure and Function of Microtubes," *Cold Spring Harbor Symposia on Quantitative Biology*, Organization of the Citoplasm, vol. XLVI, pp. 219-226 (1982).

Burris, H.A., et al., "Phase II Trial of Docetaxel and Herceptin (R) as First- or Second-Line Chemotherapy for Women with Metastatic Breast Cancer Whose Tumors Overexpress HER2," *European Journal of Cancer*, Sep. 16, 1999, 35(suppl. 4):S322, Abstract 1293.

Baselga, J., et al., "Recombinant Humanized Anti-HER2 Antibody (Herceptin™) Enhances the Antitumor Activity of Paclitaxel and Doxorubicin against HER2/*neu* Overexpressing Human Breast Cancer Xenografts," *Cancer Research*, Jul. 1, 1998, 58:2825-2831.

Baselga, J., et al., "Erratum," *Cancer Research*, Apr. 15, 1999, 59(8):2020-2021.

Baselga, J., et al., "HER2 Overexpression and Paclitaxel Sensitivity in Breast Cancer: Therapeutic Implications:" *Oncology*, Mar. 1997, 11(3)(suppl. 2):43-48.

Cobleigh, M.A., et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," *J. Clin. Oncol.*, Sep. 1999, 17(9):2639-2648.

Gianni, L., et al., "Putting Taxanes to Work in Operable Breast Cancer: A Search for Selective Indications from Empirical Studies," *Recent Results Cancer Research*, 1998, 152:314-322.

Vogel, C.L., et al., "Monotherapy of Metastatic Breast Cancer: A Review of Newer Agents," *The Oncologist*, 1999, 4:17-33.

"Are adjuvant Herceptin trials wrong?," *Scripp*, Nov. 26, 1999, 2493:21.

Corbett, T.H., et al., "Design and Evaluation of Combination Chemotherapy Trials in Experimental Animal Tumor Systems," *Cancer Treatment Reports*, May 1997, 63(5):799-801.

Munkarah A., et al., "Comparative Studies of Taxol and Taxotere on Tumor Growth and Lymphocyte Functions," *Gynecologic Oncology*, 1994, 55:211-216.

Lopes, N.M., et al., "Assessment of Microtubule Stabilizers by Semiautomated in vitro Microtubule Protein Polymerization and Mitotic Block Assays," *Cancer Chemother. Pharmacol.*, 1997, 41:37-47.

Johnson, R.A., "Taxol Chemistry. 7-O-Triflates as Precursors to Olefins and Cyclopropanes," *Tetrahedron Letters*, Oct. 10, 1994, 35(43):7893-7896.

D'Arpa, P., et al., "Topoisomerase-Targeting Antitumor Drugs," *Biochimica et Biophysica Acta*, Dec. 7, 1989, 989(2):163-177.

Gupta, R.S., et al., "Camptothecin-resistant Mutants of Chinese Hamster Ovary Cells Containing a Resistant Form of Topoisomerase I," *Cancer Research*, Nov. 15, 1988, 48(22):6404-6410.

Muggia, F.M., et al., "Phase I Clinical Trial of Weekly and Daily Treatment With Camptothecin (NSC-100880): Correlation With Preclinical Studies," *Cancer Chemotherapy Reports*, Aug. 1972, Part 1, 56(4):515-521.

Tsuruo, T., et al., "Antitumor Effect of CPT-11, a New Derivative of Camptothecin, Against Pleiotropic Drug-Resistant Tumors in vitro and in vivo," *Cancer Chemother. Pharmacol.*, Feb. 1988, 21(1):71-74.

Ringel, I., et al., "Studies with RP 56976 (Taxotere): A Semisynthetic Analogue of Taxol," *J. Natl. Cancer Inst.*, Feb. 20, 1991, 83(4):288-291.

Holmes, F.A., et al., "Phase II Trial of Taxol, an Active Drug in the Treatment of Metastatic Breast Cancer," *J. Natl. Cancer Inst.*, Dec. 18, 1991, 83(24):1797-1805.

Mäenpää, J.U., et al., "Docetaxel and Irinotecan in the Second-Line Treatment of Ovarian Cancer: Final Results of a Phase II Study," *Proceedings of American Society of Clinical Oncology*, May 18-20, 2002, 21(1):894.

Bissery, M.C., et al., "Preclinical In Vivo Evaluation of Docetaxel (Taxotere®) Containing Combinations," *Proceedings of the Cytoskeleton and Cancer*, Sep. 17-20, 1995, Abstract 50.

International Search Report, PCT/US 00/09247, Sep. 12, 2000 (corresponding to U.S. Patent No. 6,333,348).

Bissery, M.C., et al., "Experimental Antitumor Activity of Taxotere (RP 56976, NSC 628503), a Taxol Analogue," *Cancer Research*, Sep. 15, 1991, 51:4845-4852.

Corbett, T.H., et al., "Response of Transplantable Tumors of Mice to Anthracenedione Derivatives Alone and in Combination with Clinically Useful Agents," *Cancer Treatment Reports*, May 1982, 66(5):1187-1200.

Harrison, S.D., et al., "Evaluation of Combinations of Interferons and Cytotoxic Drugs in Murine Tumor Models In Vivo," *Journal of Biological Response Modifiers*, 1990, 9(4):395-400.

Lorusso, P.M., et al., "Antitumor Efficacy of Interleukin-2 Alone and in Combination with Adriamycin and Dacarbazine in Murine Solid Tumor Systems," *Cancer Research*, Sep. 15, 1990, 50:5876-5882.

Corbett, T.H., et al., "5-Fluorouracil Containing Combinations in Murine Tumor Systems," *Investigational New Drugs*, 1989, 7:37-49.

Bissery, M.C., et al., "Docetaxel (Taxotere): A Review of Preclinical and Clinical Experience. Part I: Preclinical Experience.," *Anti-Cancer Drugs*, 1995, 6:339-355.

Speicher, L.A., et al., "Combined Antimicrotubule Activity of Estramustine and Taxol in Human Prostatic Carcinoma Cell Lines," *Cancer Research*, Aug. 15, 1992, 52:443-4440.

Pierré, A., et al., "Preclinical Antitumor Activity of a New *Vinca* Alkaloid Derivative, S 12363," *Cancer Research*, May 1, 1991, 51:2312-2318.

Bayssas, M., et al., "Vindesine: A New Vinca Alkaloid," *Recent Results in Cancer Research*, 1980, 74:91-97.

English language abstract for EP 0317401.

FDA approval letter for the use of Herceptin in combination with Taxol for the first-line treatment of metastatic cancer, dated Sep. 25, 1998.

Fisherman, J., et al., "Phase I Study of Taxol Plus Doxorubicin Plus Granulocyte Colony Stimulating Factor (G-CSF) in Patients with Metastatic Breast Cancer," Abstract presented at the Second National Cancer Institute Workshop on Taxol and Taxus, Sep. 23-24, 1992.

Holmes, F.A., et al., "The M.D. Anderson Experience with Taxol in Metastatic Breast Cancer," Abstract presented at the Second National Cancer Institute Workshop on Taxol and Taxus, Sep. 23-24, 1992.

Kohn E., et al., "Phase I Trial of a Taxol Combination: Taxol, Cytoxan, and Cisplatin," Abstract presented at the Second National Cancer Institute Workshop on Taxol and Taxus, Sep. 23-24, 1992.

Tarr, B.D., et al., "A New Parenteral Vehicle for the Administration of Some Poorly Water Soluble Anti-Cancer Drugs," J. Parenter. Sci. Technol., 41(1):31-33 (1987).

Waud W.R., et al., "In Vitro and In Vivo Combination Chemotherapy Evaluations of Taxol with Doxorubicin or Topotecan," Abstract presented at the Second National Cancer Institute Workshop on Taxol and Taxus, Sep. 23-24, 1992.

METHOD OF TREATING CANCER WITH DOCETAXEL AND DOXORUBICIN

This is a continuation of application Ser. No. 10/422,823, filed Apr. 25, 2003, which is a continuation of application Ser. No. 09/705,739, filed Nov. 6, 2000, abandoned;
which is a division of application Ser. No. 09/506,902, filed Feb. 18, 2000, which issued as U.S. Pat. No. 6,239,167;
which is a division of application Ser. No. 09/371,520, filed Aug. 10, 1999, which issued as U.S. Pat. No. 6,214,863;
which is a continuation of application Ser. No. 09/182,900, filed Oct. 30, 1998, abandoned;
which is a division of application Ser. No. 08/967,036, filed Nov. 10, 1997, which issued as U.S. Pat. No. 5,908,835;
which is a division of application Ser. No. 08/424,470, filed May 9, 1995 (which is a national stage application under U.S.C. §371 of PCT/FR93/01096, filed Nov. 8, 1993), which issued as U.S. Pat. No. 5,728,687;
and claims benefit of priority of French Patent No. 92 13525, filed Nov. 10, 1992;
all of which are incorporated herein by reference.

The present invention relates to combinations of taxol, TAXOTERE (generically known as docetaxel) and their analogues and substances which are therapeutically useful in the treatment of neoplastic diseases.

Taxol, TAXOTERE and their analogues, which possess noteworthy antitumour and antileukaemic properties, are especially useful in the treatment of cancers of the ovary, breast or lung.

The preparation of taxol, TAXOTERE and their derivatives form the subject, for example, of European Patents EP 0,253, 738 and EP 0,253,739 and International Application PCT WO 92/09,589.

Generally, the doses used, which depend on factors distinctive to the subject to be treated, are between 1 and 10 mg/kg administered intraperitoneally or between 1 and 3 mg/kg administered intravenously.

It has now been found, and this forms the subject of the present invention, that the efficacy of taxol, TAXOTERE and their analogues may be considerably improved when they are administered in combination with at least one substance which is therapeutically useful in anticancer treatments and has a mechanism identical to or different from this of taxane derivatives.

Among substances which may be used in association or in combination with taxol, TAXOTERE or their analogues, there may be mentioned alkylating agents such as cyclophosphamide, isosfamide, melphalan, hexamethylmelamine, thiotepa or dacarbazine, antimetabolites such as pyrimidine analogues, for instance 5-fluorouracil and cytarabine or its analogues such as 2-fluorodeoxycytidine, or folic acid analogues such as methotrexate, idatrexate or trimetrexate, spindle poisons including vinca alkaloids such as vinblastine or vincristine or their synthetic analogues such as navelbine, or estraumestine or taxoids, epidophylloptoxins such as etoposide or teniposide, antibiotics such as daunorubicine, doxorubicin, bleomycin or mitomycin, enzymes such as L-asparaginase, topoisomerase inhibitors such as camptothecin derivates chosen from CPT-11 and topotecan or pyridobenzoindole derivatives, and various agents such as procarbazine, mitoxantrone, platinum coordination complexes such as cisplatin or carboplatin, and biological response modifiers or growth factor inhibitors such as interferons or interleukins.

Moreover, since the activity of the products depends on the doses used, it is possible to use higher doses and to increase the activity while decreasing the toxicity phenomena or delaying their onset by combining growth factors of the haematopoietic type such as G-CSF or GM-CSF or certain interleukins with taxol, TAXOTERE, their analogues or their combinations with other therapeutically active substances.

The combinations or associations according to the invention enable the phenomena of pleiotropic resistance or "multi-drug resistance" to be avoided to delayed.

More especially, the invention relates to combination of taxol, TAXOTERE and their analogues with vinca alkaloids, cyclophosphamide, 5-fluorouracil, doxorubicin, cisplatin and estoposide.

The improved efficacy of a combination according to the invention may be demonstrated by determination of the therapeutic synergy.

The efficacy of a combination according to the invention may also be characterized by adding the actions of each constituent.

A combination manifests therapeutic synergy if it is therapeutically superior to one or other of the constituents used at its optimum dose [T. H. CORBETT et al., Cancer Treatment Reports, 66, 1187 (1982)].

To demonstrate the efficacy of a combination, it may be necessary to compare the maximum tolerated dose of the combination with the maximum tolerated dose of each of the separate constituents in the study in question. This efficacy may be quantified, for example by the $\log_{10}$ cells killed, which is determined according to the following formula:

$$\log_{10} \text{ cells killed} = T - C(\text{days})/3.32 \times T_d$$

in which T–C represents the time taken for the cells to grow, which is the mean time in days for the tumours of the treated group (T) and the tumours of the treated group (C) to have reached a predetermined value (1 g for example), and $T_d$ represents the time in days needed for the volume of the tumour to double in the control animals [T. H. CORBETT et al., Cancer, 40, 2660.2680 (1977); F. M. SCHABEL et al., Cancer Drug Development, Part B, Methods in Cancer Research, 17, 3-51, New York, Academic Press Inc. (1979)]. A product is considered to be active if $\log_{10}$ cells killed is greater than or equal to 0.7. A product is considered to be very active if $\log_{10}$ cells killed is greater than 2.8.

The combination, used at its own maximum tolerated dose, in which each of the constituents will be present at a dose generally not exceeding its maximum tolerated dose, will manifest therapeutic synergy when the $\log_{10}$ cells killed is greater than the value of the $\log_{10}$ cells killed of the best constituent when it is administered alone.

The efficacy of the combinations on solid tumours may be determined experimentally in the following manner:

The animals subjected to the experiment, generally mice, are subcutaneously grafted bilaterally with 30 to 60 mg of a tumour fragment on day 0. The animals bearing tumours are mixed before being subjected to the various treatments and controls. In the case of treatment of advanced tumours, tumours are allowed to develop to the desired size, animals having the insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. The different animal groups are weighed 3 or 4 times a week until the maximum weight loss is attained, and the groups are then weighed at least once a week until the end of the trial.

The tumours are measured 2 or 3 times a week until the tumour reaches approximately 2 g, or until the animal dies if this occurs before the tumour reaches 2 g. The animals are autopsied when sacrificed.

The antitumour activity is determined in accordance with the different parameters recorded.

For a study of the combinations on leukaemias, the animals are grafted with a particular number of cells, and the antitumour activity is determined by the increase in the survival time of the treated mice relative to the controls. The product is considered to be active if the increase in survival time is greater than 27%, and is considered to be very active if it is greater than 75% in the case of P388 leukaemia.

The results obtained with combinations of TAXOTERE and various chemotherapeutic agents, such as cyclophosphamide (alkylating agent), 5-fluorouracil (antimetabolite), etoposide (semisynthetic podophyllotoxin agent) and vincristine (vinca alkaloid), the combinations being used at their optimum dose, are given as examples in the following tables.

TABLE 1

Activity of the combination Taxotere + cyclophosphamide at the optimum dose against advanced MA13/c mammary adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 15 | 14, 17, 20 | 45 | 2.8 |
| Cylcophosphamide | 118 | 14 | 118 | 1.3 |
| Taxotere + cylcophosphamide | 7.5 90.0 | 14, 17, 20, 14 | 22.5 90 | 3.4 |

TABLE 2

Activity of the combination Taxotere + etoposide at the optimum dose against early B16 melanoma grafted subcutaneously

| Product | Dose mg/kg/injection i.v. | Administration on days: | Total dose mg/kg | $\log_{10}$ cells killed |
|---|---|---|---|---|
| Taxotere | 17.5 | 4, 7, 10, 13 | 70 | 2.8 |
| Etoposide | 46.2 | 4, 7, 10, 13 | 184.8 | 2.8 |
| Taxotere + etoposide | 15.7 13.8 | 4, 7, 10, 13 (simultaneous) | 62.8 55.2 | 4.1 |

TABLE 3

Activity of the combination Taxotere + 5-fluorouracil at the optimum dose against advanced C38 colon adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 22 | 21, 25, 29, 33 | 88.0 | 1.4 |
| 5-fluorouracil | 43.4 | 21, 25, 29, 33 | 173.6 | 1.1 |
| Taxotere + 5-fluorouracil | 17.6 27.0 | 21, 25, 29, 33 (simultaneous) | 70.4 108.0 | 4.8 |

TABLE 4

Activity of the combination Taxotere + vincristine at the optimum dose against P388 leukaemia ($10^6$ cells i.p.)

| Product | Dose mg/kg/injection i.v. | Administration on days: | Total dose mg/kg | $\log_{10}$ cells killed |
|---|---|---|---|---|
| Taxotere | 21.7 | 4, 7, 10 | 65.1 | 15 |
| vincristine | 1.2 | 4, 7, 10 | 3.6 | 46 |
| Taxotere + vincristine | 21.75 1.2 | 1, 4, 7 (simultaneous) | 65.25 3.6 | 62 |
| Taxotere + vincristine | 21.75 1.2 | 1, 4, 7 (4 hours apart) | 65.25 3.6 | 77 |

The present invention also relates to pharmaceutical compositions containing the combinations according to the invention.

The products of which the combinations are composed may be administered simultaneously, separately or spaced out over a period of time so as to obtain the maximum efficacy of the combination; it being possible for each administration to vary in its duration from a rapid administration to a continuous perfusion.

As a result, for the purposes of the present invention, the combinations are not exclusively limited to those which are obtained by physical association of the constituents, but also to those which permit a separate administration, which can be simultaneous or spaced out over a period of time.

The compositions according to the invention are preferably compositions which can be administered parentally. However, these compositions may be administered orally or intraperitoneally in the case of localized regional therapies.

The compositions for parental administration are generally phaimaceutically acceptable, sterile solutions or suspensions which may optionally be prepared as required at the time of use. For the preparation of non-aqueous solutions or suspensions, natural vegetable oils such as olive oil, sesame oil or liquid petroleum or injectable organic esters such as ethyl oleate may be used. The sterile aqueous solutions can consist of a solution of the product in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely effect the composition. The combinations may also take the form of liposomes or the form of an association with carriers as cyclodextrins or polyethylene glycols.

The compositions for oral or intraperitoneal administration are preferably aqueous suspensions or solutions.

In the combinations according to the invention, the application of the constituents of which may be simultaneous, separate or spaced out over a period of time, it is especially advantageous for the amount of taxane derivative to represent from 10 to 90% by weight of the combination, it being possible for this content to vary in accordance with the nature of the associated substance, the efficacy sought and the nature of the cancer to be treated.

The combinations according to the invention are especially useful in the treatment of cancers of the breast, ovary or lung. In particular, they can afford the advantage of being able to employ the constituents at considerably lower doses than those at which they are used alone.

The example which follows illustrates a combination according to the invention.

EXAMPLE 10-cm³ ampoules containing 100 mg of TAXOTERE are prepared, for intravenous administration, according to the usual technique.

5-cm³ ampoules containing 100 mg of estoposide are prepared, for intravenous administration, according to the usual technique.

These solutions are administered simultaneously, after appropriate dilution, by perfusion.

The treatment may be repeated several times daily or weakly until there is a partial or total remission or a cure.

The invention claimed is:

1. A method of treating a cancer in a human patient comprising administering an effective amount of a combination of docetaxel and doxorubicin to the patient, wherein the combination of docetaxel and doxorubicin has greater anticancer activity in the human patient than the optimum dose of docetaxel alone against said cancer in the human patient or the optimum dose of doxorubicin alone against said cancer in the human patient.

2. The method of claim 1, wherein docetaxel and doxorubicin are each present in a separate pharmaceutically acceptable composition and the compositions are administered simultaneously.

3. The method of claim 1, wherein docetaxel and doxorubicin are each present in a separate pharmaceutically acceptable composition and the compositions are administered sequentially.

4. The method of claim 1, wherein the cancer is lung cancer.

5. The method of claim 1, wherein the cancer is breast cancer.

6. The method of claim 1, wherein the cancer is ovarian cancer.

7. The method of claim 1, wherein the cancer is adenocarcinoma.

8. The method of claim 1, wherein the cancer is melanoma.

9. The method of claim 1, wherein the cancer is leukemia.

10. The method of claim 1, wherein the docetaxel and doxorubicin are each administered parenterally or intraperitoneally.

11. The method of claim 1, wherein the docetaxel and doxorubicin are each administered intravenously.

12. A method of treating a cancer in a human patient according to claim 1, wherein the combination of docetaxel and doxorubicin has greater anticancer activity in the human patient than the optimum dose of docetaxel alone against said cancer in the human patient.

13. A method of treating a cancer in a human patient comprising administering an effective amount of a combination of docetaxel and doxorubicin to the patient, wherein the combination of docetaxel and doxorubicin has greater anticancer activity in the human patient than the maximum tolerated dose of docetaxel alone against said cancer in the human patient or the maximum tolerated dose of doxorubicin alone against said cancer in the human patient.

14. A method of treating a cancer in a human patient according to claim 13, wherein the combination of docetaxel and doxorubicin has greater anticancer activity in the human patient than the maximum tolerated dose of docetaxel alone against said cancer in the human patient.

15. A method of treating a cancer in a human patient according to claim 1, wherein the combination of docetaxel and doxorubicin has greater anticancer activity in the human patient than the optimum dose of doxorubicin alone against said cancer in the human patient.

16. A method of treating a cancer in a human patient according to claim 13, wherein the combination of docetaxel and doxorubicin has greater anticancer activity in the human patient than the maximum tolerated dose of doxorubicin alone against said cancer in the human patient.

17. A method of treating a cancer in a human patient comprising administering an effective amount of a combination of the drugs docetaxel and doxorubicin to the patient, wherein the combination of the drugs docetaxel and doxorubicin has greater anticancer activity in the human patient than the optimum dose of each drug alone against said cancer in the human patient.

18. A method of treating a cancer in a human patient comprising administering an effective amount of a combination of the drugs docetaxel and doxorubicin to the patient, wherein the combination of the drugs docetaxel and doxorubicin has greater anticancer activity in the human patient than the maximum tolerated dose of each drug alone against said cancer in the human patient.

* * * * *

UNITED STATES PATENT AND TRADEMARK OFFICE
CERTIFICATE OF CORRECTION

| | | |
|---|---|---|
| PATENT NO. | : 7,994,212 B2 | Page 1 of 1 |
| APPLICATION NO. | : 10/747206 | |
| DATED | : August 9, 2011 | |
| INVENTOR(S) | : Marie-Christine Bissery et al. | |

It is certified that error appears in the above-identified patent and that said Letters Patent is hereby corrected as shown below:

Claim 12, col. 6, lines 1-5, delete claim 12 and insert therefor:

--12. A method of treating a cancer in a human patient comprising administering a combination of docetaxel and doxorubicin to the patient, wherein the combination of docetaxel and doxorubicin has greater anticancer activity in the human patient than the optimum dose of docetaxel alone against said cancer in the human patient and the optimum dose of doxorubicin alone against said cancer in the human patient.--.

Claim 14, col. 6, lines 14-18, delete claim 14 and insert therefor:
--14. A method of treating a cancer in a human patient comprising administering a combination of docetaxel and doxorubicin to the patient, wherein the combination of docetaxel and doxorubicin has greater anticancer activity in the human patient than the maximum tolerated dose of docetaxel alone against said cancer in the human patient and the maximum tolerated dose of doxorubicin alone against said cancer in the human patient.--.

Delete claims 15, 16, 17, and 18 in their entirety.

Signed and Sealed this
Twentieth Day of December, 2011

David J. Kappos
*Director of the United States Patent and Trademark Office*

UNITED STATES PATENT AND TRADEMARK OFFICE
CERTIFICATE OF CORRECTION

PATENT NO.       : 7,994,212 B2
APPLICATION NO.  : 10/747206
DATED            : August 9, 2011
INVENTOR(S)      : Marie-Christine Bissery et al.

It is certified that error appears in the above-identified patent and that said Letters Patent is hereby corrected as shown below:

Delete the title page and substitute therefore the attached title page showing the corrected number of claims in patent.

Claim 12, col. 6, lines 1-5, delete claim 12 and insert therefore:

--12. A method of treating a cancer in a human patient comprising administering a combination of docetaxel and doxorubicin to the patient, wherein the combination of docetaxel and doxorubicin has greater anticancer activity in the human patient than the optimum dose of docetaxel alone against said cancer in the human patient and the optimum dose of doxorubicin alone against said cancer in the human patient.--.

Claim 14, col. 6, lines 14-18, delete claim 14 and insert therefore:

--14. A method of treating a cancer in a human patient comprising administering a combination of docetaxel and doxorubicin to the patient, wherein the combination of docetaxel and doxorubicin has greater anticancer activity in the human patient than the maximum tolerated dose of docetaxel alone against said cancer in the human patient and the maximum tolerated dose of doxorubicin alone against said cancer in the human patient.--.

Column 6, lines 19-42, delete claims 15, 16, 17, and 18 in their entirety.

This certificate supersedes the Certificate of Correction issued December 20, 2011.

Signed and Sealed this
Tenth Day of January, 2012

David J. Kappos
*Director of the United States Patent and Trademark Office*

(12) United States Patent
Bissery

(10) Patent No.: US 7,994,212 B2
(45) Date of Patent: Aug. 9, 2011

(54) METHOD OF TREATING CANCER WITH DOCETAXEL AND DOXORUBICIN

(75) Inventor: Marie-Christine Bissery, Vitry Sur Seine (FR)

(73) Assignee: Aventis Pharma S.A., Antony (FR)

( * ) Notice: Subject to any disclaimer, the term of this patent is extended or adjusted under 35 U.S.C. 154(b) by 1401 days.

(21) Appl. No.: 10/747,206

(22) Filed: Dec. 30, 2003

(65) Prior Publication Data

US 2004/0152642 A1    Aug. 5, 2004

Related U.S. Application Data

(60) Continuation of application No. 10/422,823, filed on Apr. 25, 2003, which is a continuation of application No. 09/705,739, filed on Nov. 6, 2000, now abandoned, which is a division of application No. 09/506,902, filed on Feb. 18, 2000, now Pat. No. 6,239,167, which is a division of application No. 09/371,520, filed on Aug. 10, 1999, now Pat. No. 6,214,863, which is a continuation of application No. 09/182,900, filed on Oct. 30, 1998, now abandoned, which is a division of application No. 08/967,036, filed on Nov. 10, 1997, now Pat. No. 5,908,835, which is a division of application No. 08/424,470, filed as application No. PCT/FR93/01096 on Nov. 8, 1993, now Pat. No. 5,728,687.

(30) Foreign Application Priority Data

Nov. 10, 1992 (FR) ................... 92 13525

(51) Int. Cl.
*A01N 43/02* (2006.01)
*A61K 31/436* (2006.01)

(52) U.S. Cl. .................... 514/449; 514/283; 540/478

(58) Field of Classification Search .............. None
See application file for complete search history.

(56) References Cited

U.S. PATENT DOCUMENTS

| | | |
|---|---|---|
| 4,206,221 A | 6/1980 | Miller et al. |
| 4,814,470 A | 3/1989 | Colin et al. |
| 4,857,653 A | 8/1989 | Colin et al. |
| 4,876,399 A | 10/1989 | Holton et al. |
| 4,892,735 A | 1/1990 | Harrap |
| 5,015,744 A | 5/1991 | Holton |
| 5,136,060 A | 8/1992 | Holton |
| 5,229,526 A | 7/1993 | Holton |
| 5,254,580 A | 10/1993 | Chen et al. |
| 5,262,409 A | 11/1993 | Margolis et al. |
| 5,294,637 A | 3/1994 | Chen et al. ............ 514/559 |
| 5,294,737 A | 3/1994 | Ojima |
| 5,466,834 A | 11/1995 | Holton |
| 5,476,954 A | 12/1995 | Bourzat et al. |
| 5,494,683 A | 2/1996 | Liversidge et al. |
| 5,532,388 A | 7/1996 | Bouchard et al. ......... 549/510 |
| 5,645,988 A | 7/1997 | Vande Woude et al. |
| 5,728,687 A | 3/1998 | Bissery |
| 5,814,658 A | 9/1998 | Bouchard et al. ......... 514/49 |
| 5,908,835 A | 6/1999 | Bissery |
| 6,214,863 B1 | 4/2001 | Bissery |
| 6,239,167 B1 | 5/2001 | Bissery |
| 6,441,026 B1 | 8/2002 | Bissery |

FOREIGN PATENT DOCUMENTS

| | | |
|---|---|---|
| EP | 0317401 | 5/1989 |
| EP | 738 253 | 6/1995 |
| EP | 0 827 745 A1 | 3/1998 |
| EP | 0 827 745 B1 | 3/1998 |
| EP | 0 982 028 A1 | 3/2000 |
| WO | WO 92/09589 | 6/1992 |
| WO | WO 92/19765 | 11/1992 |
| WO | WO 94/10995 | 5/1994 |
| WO | WO 94/13654 | 6/1994 |
| WO | WO 94/13655 | 6/1994 |
| WO | WO 97/38731 | 10/1997 |
| WO | WO 99/31140 | 6/1999 |

OTHER PUBLICATIONS

Guéritte-Voegelein et al., "Relationships between the Structure of Taxol Analogues and Their Antimitotic Activity," *J. Med. Chem.* 34:992-998 (1991).
Commerçon et al., "Tetrahedron Letters," 33(36):5185-5188 (1992).
Chen et al., "Serendipitous Synthesis of a Cyclopropane-Containing Taxol Analog Via Anchimeric Participation of an Unactivated Angular Methyl Group," *J. Org. Chem.*, 58:4520-4521 (1993).
Klein et al., "Synthesis of Ring B-Rearranged Taxane Analogs," *J. Org. Chem.*, 59: 2370-2373 (1994).
Rowinsky, E., et al., "The Clinical Pharmacology and Use of Antimicrotubule Agents in Cancer Chemotherapeutics," *Pharmac. Ther.*, vol. 52, pp. 35-84 (1991).
Rowinsky, E. et al., "Sequences of Taxol and Cisplatin: A Phase I and Pharmacologic Study," *J. of Clin. Oncology*, vol. 9, No. 9, pp. 1692-1703 (1991).
Bissery, M., et al., Abstract 2645, *Proceedings of the AACR*, vol. 33, p. 443 (Mar. 1992).
Bissery, M., et al., "Preclinical Profile of Docetaxel (Taxotere): Efficacy as a Single Agent and in Combination," *Seminars in Oncology*, vol. 22, No. 6 (Suppl 13), pp. 3-16 (1995).
Bissery, M., et al., Abstract 1599, "Preclinical In Vivo Activity of Docetaxel Containing Combinations," *Proceedings of ASCO*, vol. 14, p. 489 (1995).
Bissery, M., et al., "The Taxoids," *Cancer Therapeutics: Experimental and Clinical Agents*, Chapter 8, pp. 175-193 (1997).
Mirabelli, C., et al., "A Murine Model to Evaluate the Ability of In Vitro Clonogenic Assays to Predict the Response to Tumors In Vivo," *Cancer Res.*, vol. 48, pp. 5447-5454 (1988).
Llombart-Cussac, A., et al., Proceedings of ASCO, vol. 16 (1997), Abstract No. 629.

(Continued)

*Primary Examiner* — Irene Marx
(74) *Attorney, Agent, or Firm* — Finnegan, Henderson, Farabow, Garrett & Dunner LLP

(57) ABSTRACT

Antitumor combinations comprising a taxane and at least one antibiotic for treating neoplastic diseases are described.

14 Claims, No Drawings